(12) United States Patent
Imajo et al.

(10) Patent No.: US 10,791,953 B2
(45) Date of Patent: Oct. 6, 2020

(54) HEADWEAR FOR ELECTROENCEPHALOGRAPHY

(71) Applicant: NIHON KOHDEN CORPORATION, Shinjuku-ku, Tokyo (JP)

(72) Inventors: Kaoru Imajo, Tokyo (JP); Shogo Shirasaka, Tokyo (JP); Yasushi Okitsu, Tokyo (JP); Satoru Uchinuma, Tokyo (JP); Norihide Shimizu, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 142 days.

(21) Appl. No.: 15/570,175

(22) PCT Filed: May 16, 2016

(86) PCT No.: PCT/JP2016/002391
§ 371 (c)(1),
(2) Date: Oct. 27, 2017

(87) PCT Pub. No.: WO2016/185707
PCT Pub. Date: Nov. 24, 2016

(65) Prior Publication Data
US 2018/0132746 A1 May 17, 2018

(30) Foreign Application Priority Data
May 21, 2015 (JP) ................. 2015-103603

(51) Int. Cl.
*A61B 5/0476* (2006.01)
*A61B 5/00* (2006.01)
(52) U.S. Cl.
CPC .......... *A61B 5/0476* (2013.01); *A61B 5/4064* (2013.01); *A61B 5/6803* (2013.01); *A61B 5/6814* (2013.01); *A61B 5/6831* (2013.01)

(58) Field of Classification Search
CPC ... A61B 5/0476; A61B 5/4064; A61B 5/6803; A61B 5/6814; A61B 5/6831; A61B 5/00; A61B 5/0478
See application file for complete search history.

(56) References Cited

U.S. PATENT DOCUMENTS 3,998,213 A * 12/1976 Price .................... A61B 5/0424
600/383
4,928,696 A * 5/1990 Henderson ........... A61B 5/0478
600/383
(Continued)

FOREIGN PATENT DOCUMENTS

CN 102458242 A 5/2012
EP 0 541 393 A1 5/1993
(Continued)

OTHER PUBLICATIONS

Search Report dated Aug. 29, 2016 by the International Searching Authority in counterpart International Patent Application No. PCT/JP2016/002391 (PCT/ISA/210).
(Continued)

*Primary Examiner* — Linda C Dvorak
*Assistant Examiner* — Annabeth E Rodriguez
(74) *Attorney, Agent, or Firm* — Sughrue Mion, PLLC

(57) ABSTRACT

A headwear for electroencephalography is provided. The headwear includes a first arm to be attached to an area extending from a forehead or an occiput of a subject to a top of a head of the subject and configured to hold a first electroencephalogram electrode, a second arm connected to the first arm to be attached to a lateral side of the head of the subject and configured to hold a second electroencephalogram electrode, a third arm connected to the first arm to be attached to another lateral side of the head of the subject and configured to hold a third electroencephalogram electrode, a stretchable support member connectable to the first to third (Continued)

arms to cover at least a portion of the head in a direction toward the first arm, and at least one adjusting mechanism to adjust tightness of the first to third arms to the head.

18 Claims, 10 Drawing Sheets

(56) References Cited

U.S. PATENT DOCUMENTS

| | | | |
|---|---|---|---|
| 5,293,867 A | 3/1994 | Oommen | |
| 5,479,934 A * | 1/1996 | Imran | A61B 5/0017 600/390 |
| 5,800,351 A | 9/1998 | Mann | |
| 2005/0197556 A1* | 9/2005 | Stoler | A61B 5/0476 600/383 |
| 2007/0225585 A1* | 9/2007 | Washbon | A61B 5/0478 600/393 |
| 2007/0235716 A1 | 10/2007 | Delic et al. | |
| 2007/0238945 A1 | 10/2007 | Delic et al. | |
| 2012/0190959 A1 | 7/2012 | Hayakawa et al. | |
| 2012/0226127 A1* | 9/2012 | Asjes | A61B 5/04085 600/383 |
| 2014/0257073 A1* | 9/2014 | Machon | A61B 5/04012 600/383 |
| 2014/0276183 A1 | 9/2014 | Badower | |
| 2015/0133762 A1 | 5/2015 | Hayakawa et al. | |
| 2015/0282760 A1* | 10/2015 | Badower | A61B 5/04012 600/383 |
| 2018/0014740 A1 | 1/2018 | Hayakawa et al. | |

FOREIGN PATENT DOCUMENTS

| | | | |
|---|---|---|---|
| JP | 2007-296266 A | | 11/2007 |
| JP | 2009-530064 A | | 8/2009 |
| JP | 2014-176748 A | | 9/2014 |
| JP | 2014176748 A | * | 9/2014 |
| WO | 2015/033440 A1 | | 1/1919 |
| WO | 2014/145487 A1 | | 9/2014 |
| WO | 2014/158803 A1 | | 10/2014 |

OTHER PUBLICATIONS

Written Opinion dated Aug. 29, 2016 by the International Searching Authority in counterpart International Patent Application No. PCT/JP2016/002391 (PCT/ISA/237).

Office Action dated Jan. 29, 2019 by the Japanese Patent Office in counterpart Japanese Patent Application No. 2015-103603.

Communication dated Nov. 18, 2019, issued by the State Intellectual Property Office of P.R. China in counterpart Chinese Application No. 201680029496.2.

Communication dated Jul. 3, 2020 issued by the State Intellectual Property Office of P.R. China in counterpart Chinese Application No. 201680029496.2.

* cited by examiner

[Fig. 1]
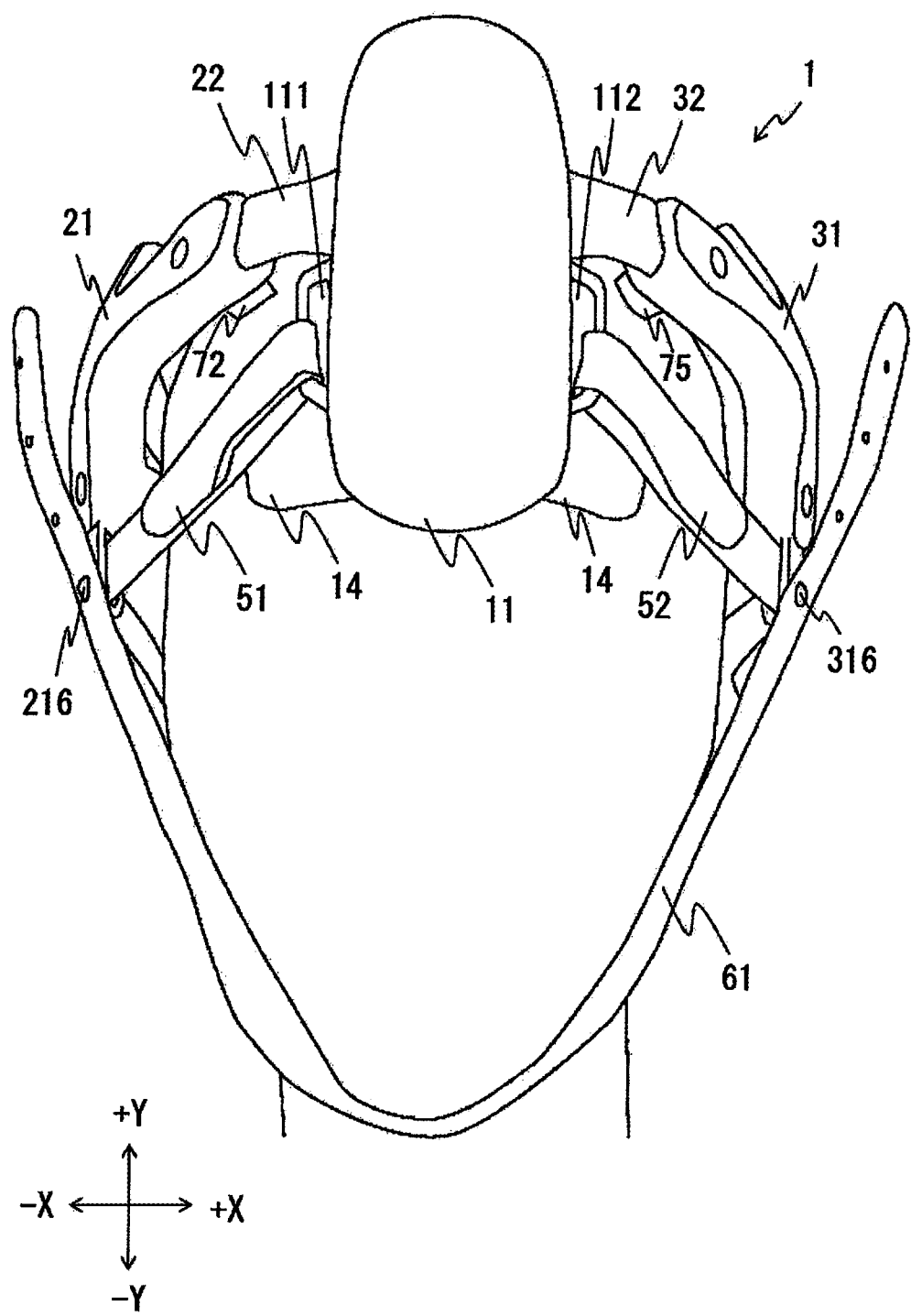

[Fig. 2]
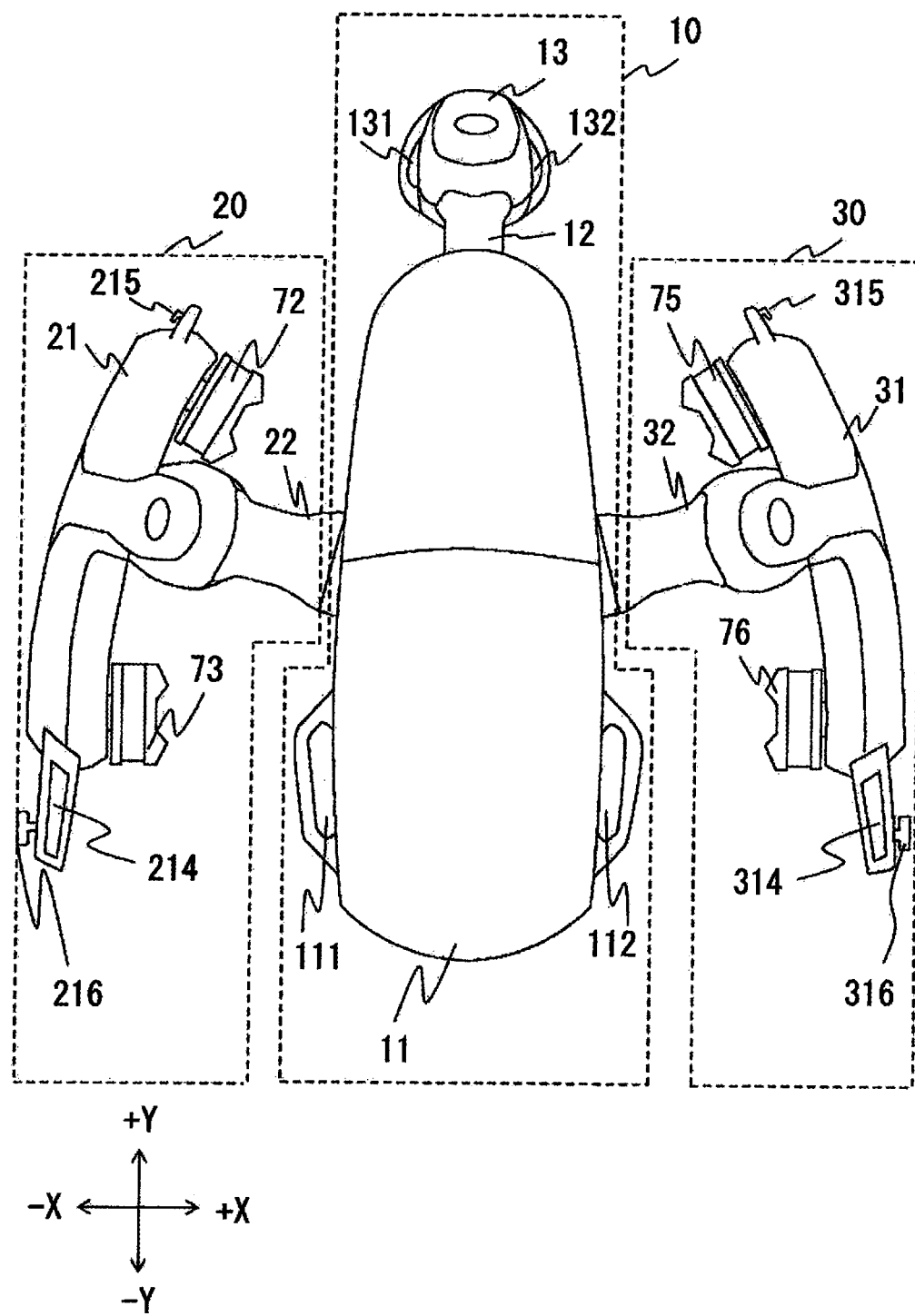

[Fig. 3]
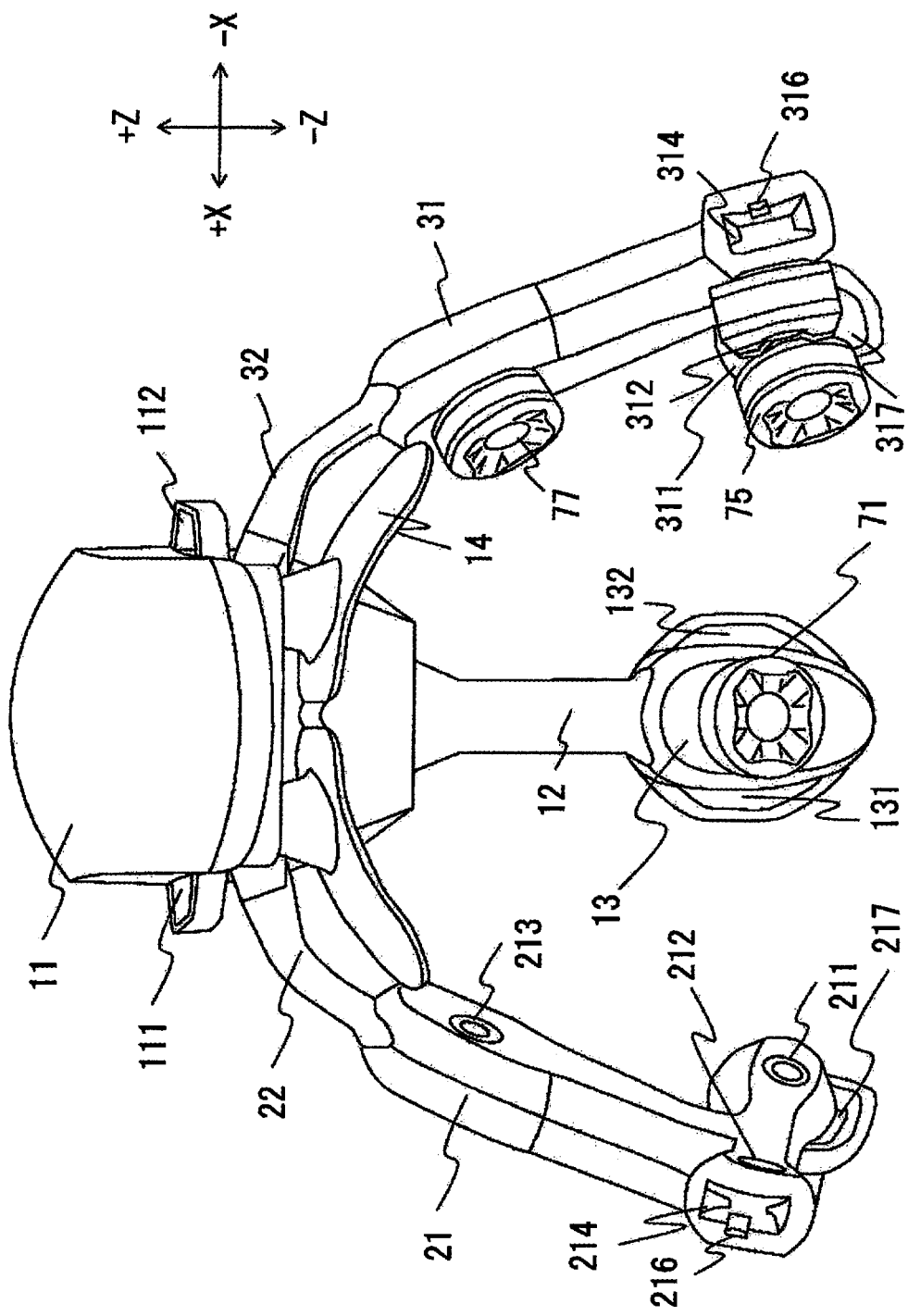

[Fig. 4]
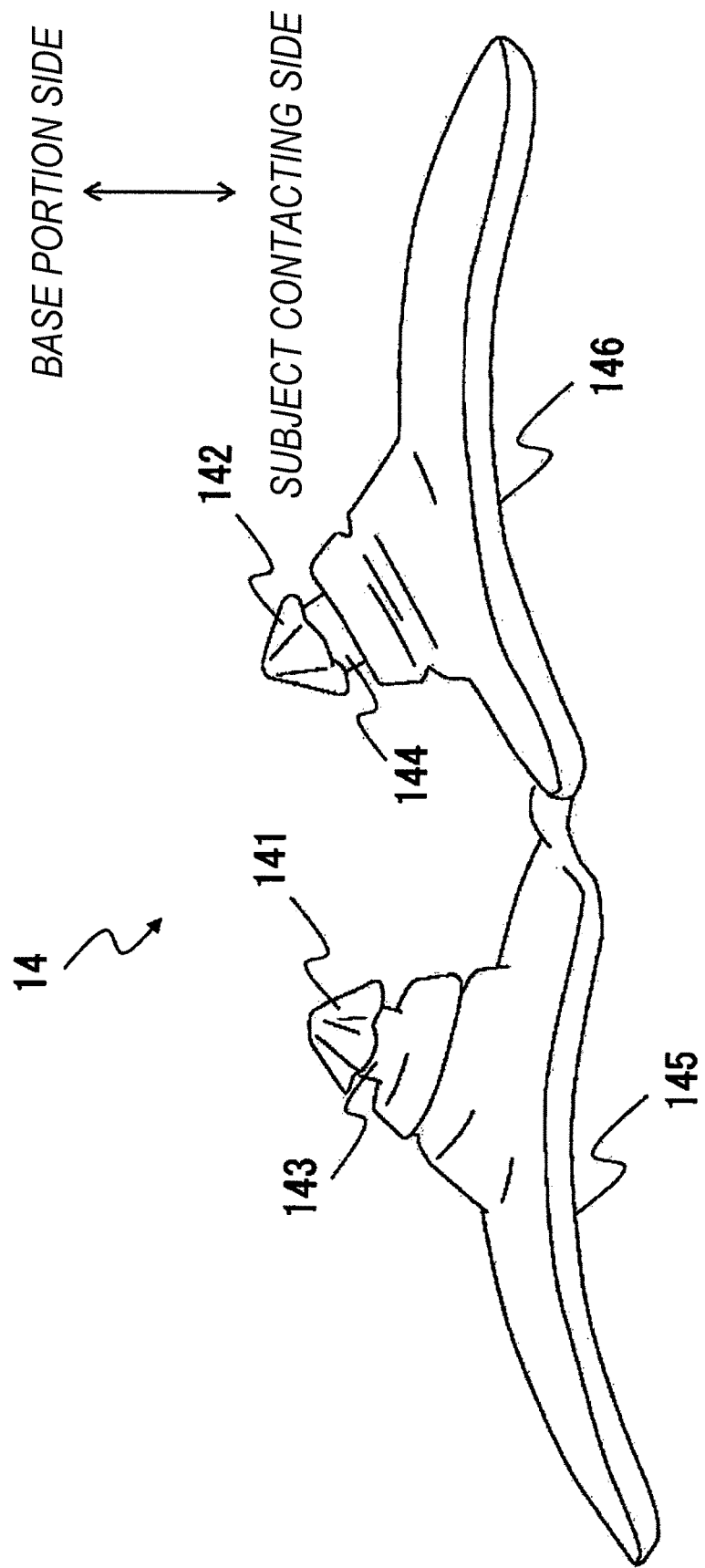

[Fig. 5]
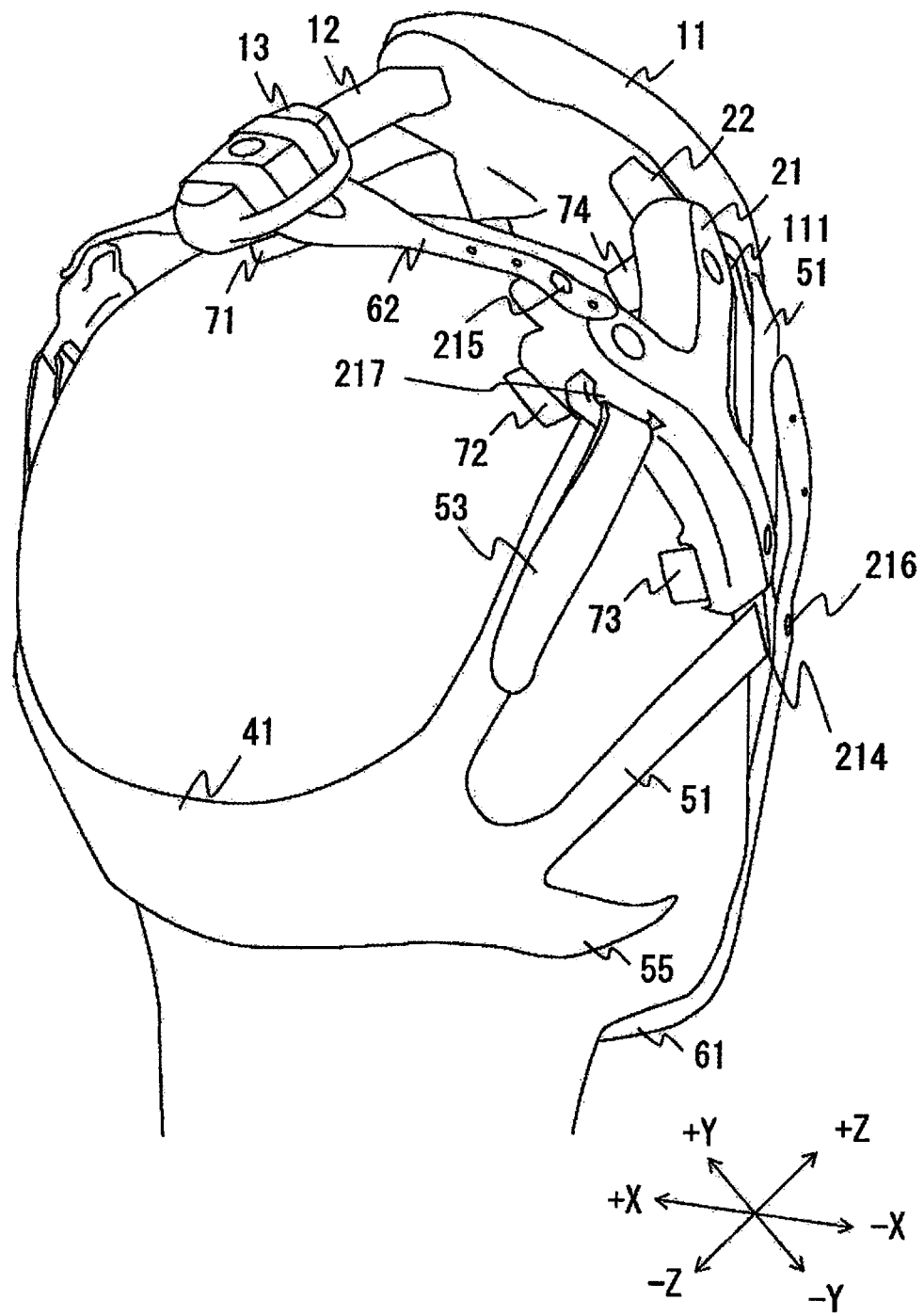

[Fig. 6]
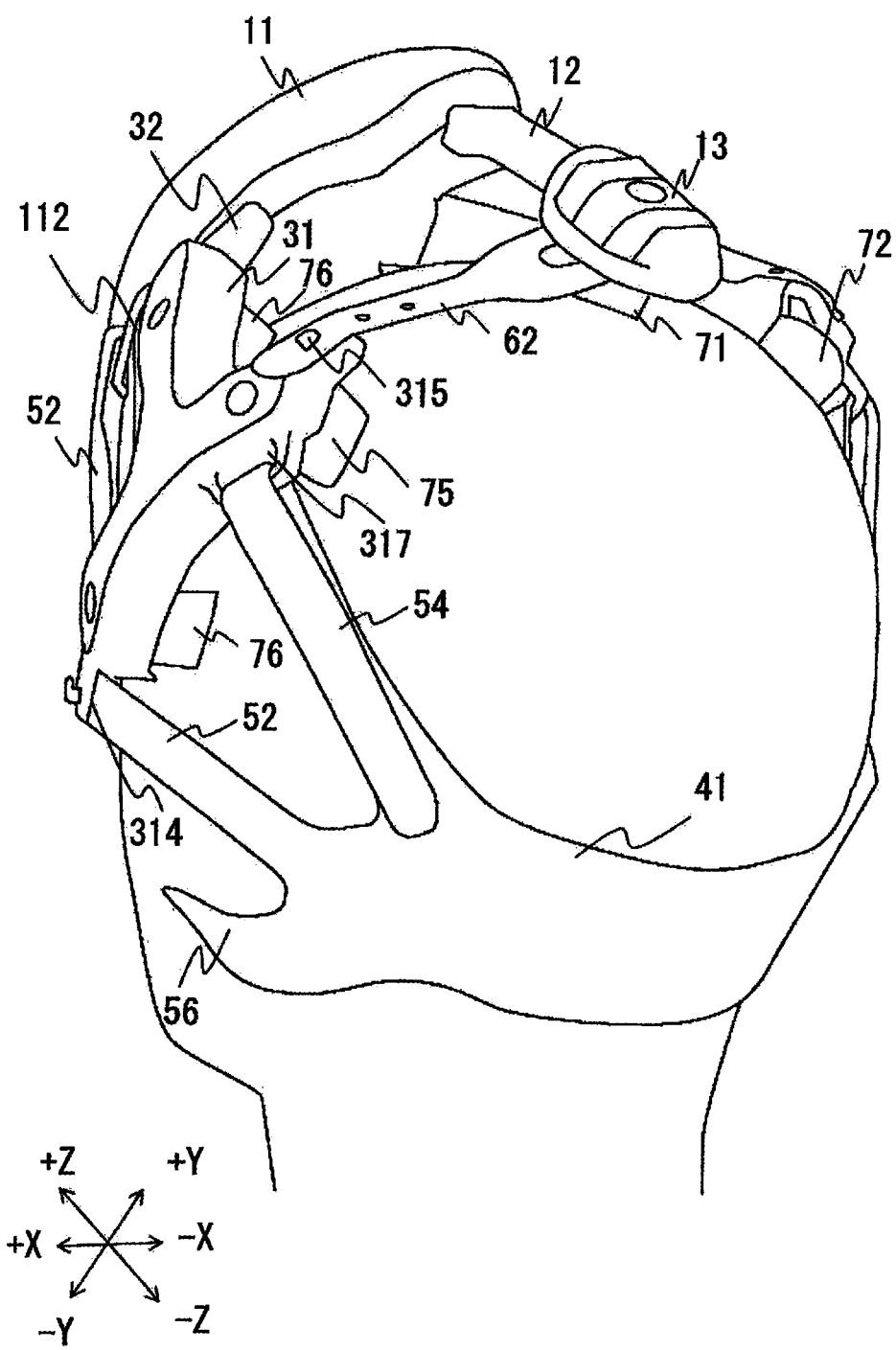

[Fig. 7]
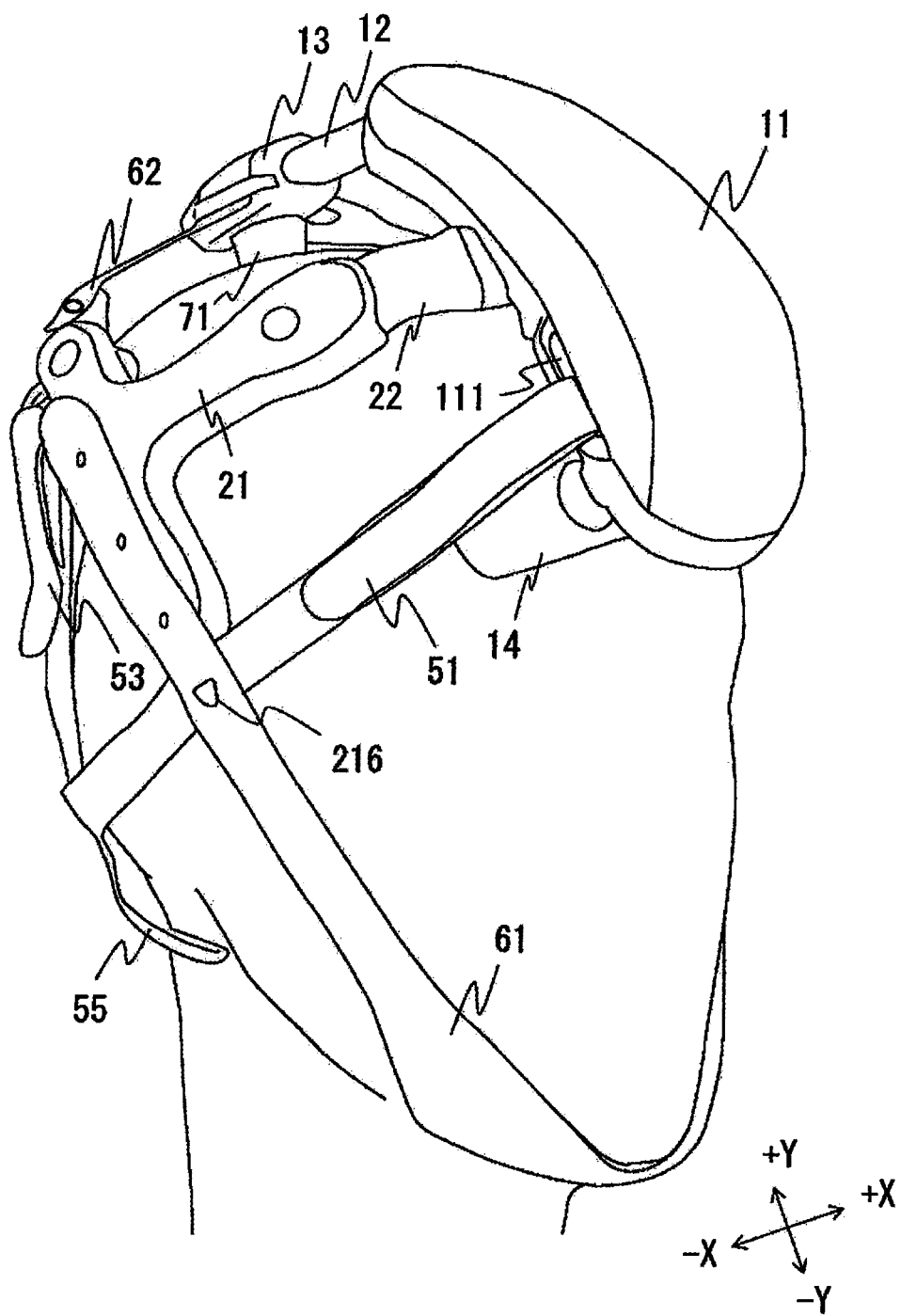

[Fig. 8]
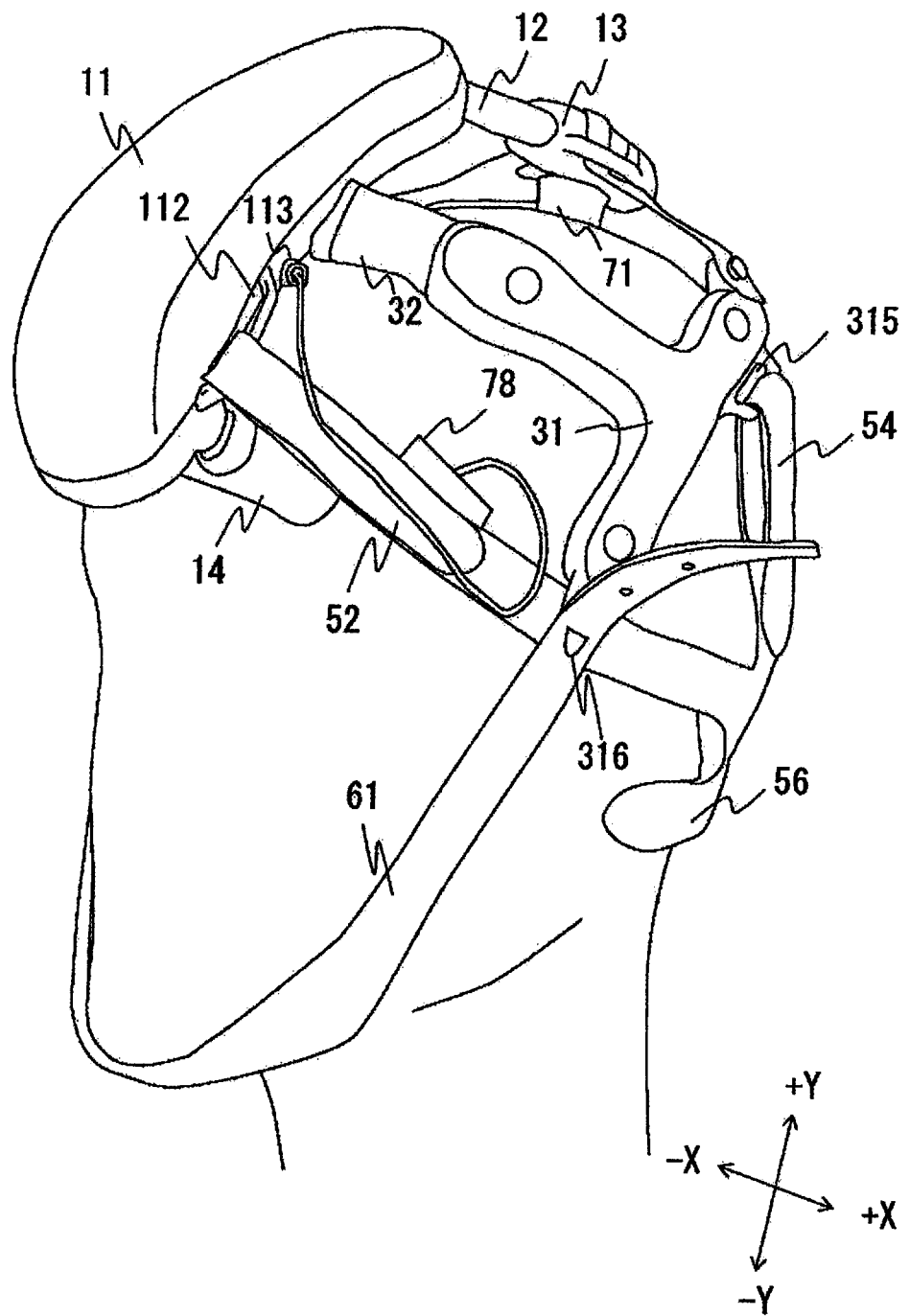

[Fig. 9]
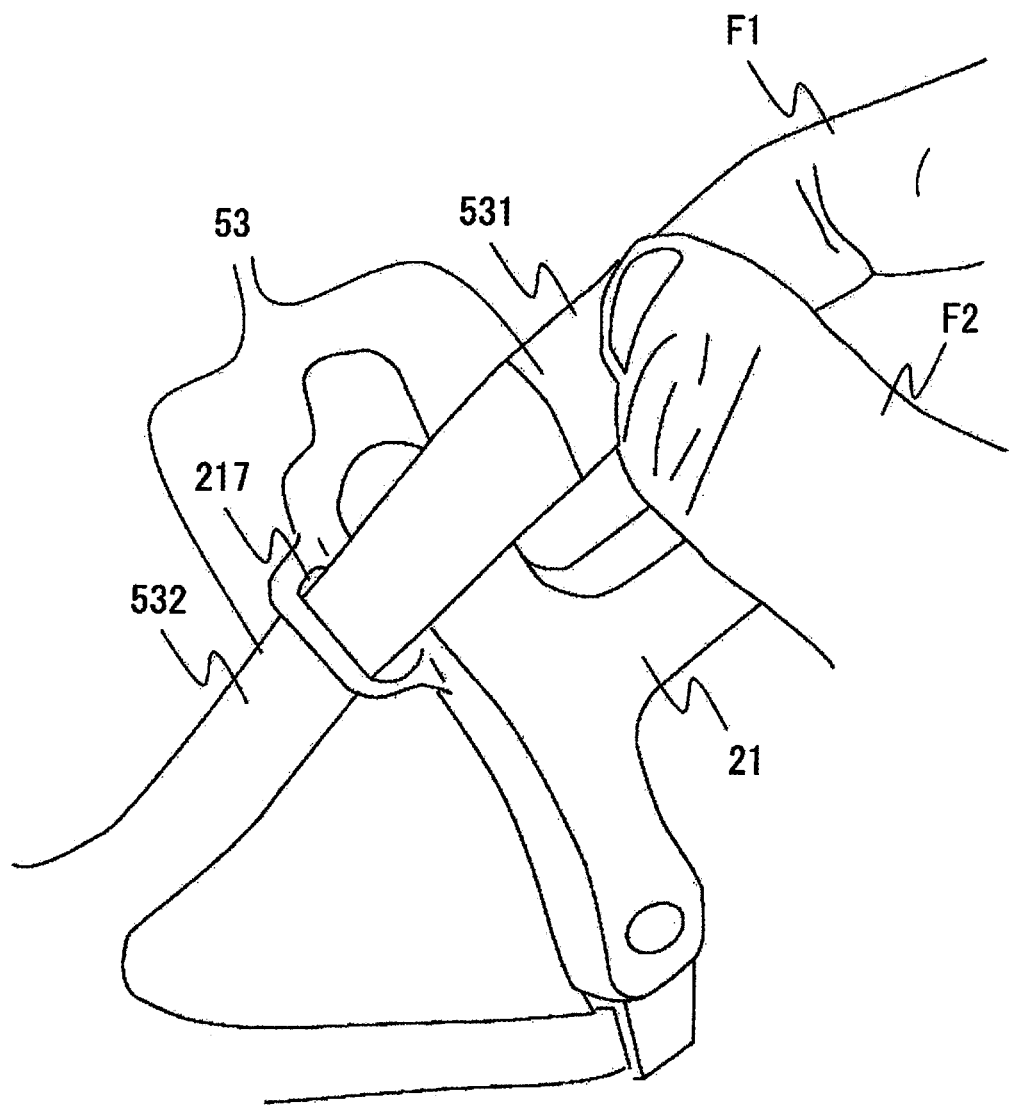

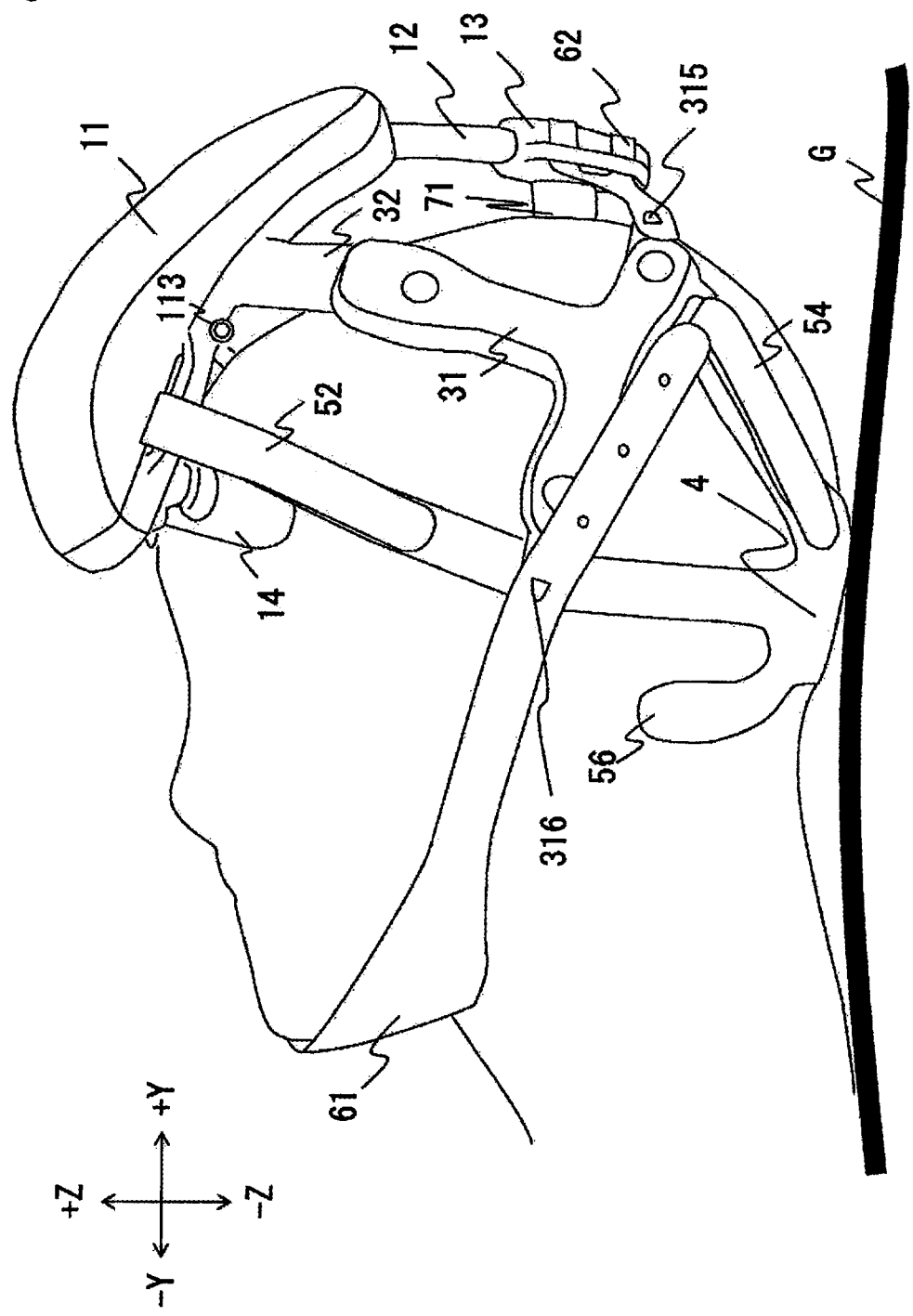
[Fig. 10]

HEADWEAR FOR ELECTROENCEPHALOGRAPHY

TECHNICAL FIELD

The present invention relates to a headwear for electroencephalography (EEG).

BACKGROUND ART

Brain waves are electric signals generated by activities of a human brain, and can be measured by a measuring apparatus (electroencephalograph) using electroencephalogram electrodes (EEG electrodes) attached to a scalp of a subject. Brain waves to be measured vary depending on a location on the scalp. Therefore, an operator attaches the EEG electrodes at predetermined locations on the scalp to perform an EEG. That is, many EEG electrodes need to be attached at respective predetermined locations on the scalp. The International 10/20 system is an example of EEG electrode arrangement.

Recently, an EEG is expected to be used in a diagnosis not only in the field of brain function test but also in the field of emergency medicine. As described above, EEG electrodes need to be placed at their respective predetermined positions in accordance with, for example, the International 10/20 system. However, unskilled staff takes a long time to attach the EEG electrodes at their respective predetermined positions. Following are related art headset or head cap for facilitating the attachment of the EEG electrodes to their predetermined positions.

U.S. Pat. No. 5,293,867A discloses an EEG head cap having a plurality of straps made of stretchable material and sewn to one another to be in a form like a lattice. On the straps, position locations for EEG electrodes are arranged on the straps at locations corresponding to at the predetermined positions according to the International 10/20 system.

JP2009-530064A discloses a flexible and rigid electrode headset for placing electrodes. The flexibility of the electrode headset enables the electrodes to be firmly attached to a head of a subject.

The head cap of U.S. Pat. No. 5,293,867A uses the stretchability of the material to firmly attach the EEG electrodes to a scalp of a subject. Likewise, the electrode headset of JP2009-530064A uses its flexibility to firmly attach the EEG electrodes to a scalp of a subject. However, heads of subjects have various sizes. Therefore, even with the headset (or the head cap) made of a stretchable (or flexible) material, it may be too tight or electrodes may not be in sufficient contact, depending on a size of a head of a subject.

SUMMARY

Illustrative aspects of the present invention provide a headwear for electroencephalography with which EEG electrodes can be attached at suitable locations in accordance with a size of a head of a subject.

According to an illustrative aspect of the present invention, a headwear for electroencephalography is provided. The headwear includes a first arm to be attached to an area extending from a forehead or an occiput of a subject to a top of a head of the subject, the first arm being configured to hold at least a first electroencephalogram electrode, a second arm to be attached to a lateral side of the head of the subject, the second arm being connected to the first arm and configured to hold at least a second electroencephalogram electrode, a third arm to be attached to another lateral side of the head of the subject, the third arm being connected to the first arm and configured to hold at least a third electroencephalogram electrode, a stretchable support member connectable to the first to third arms to cover at least a portion of the head of the subject in a direction toward the first arm, and at least one adjusting mechanism configured to adjust tightness of the first to third arms to the head.

BRIEF DESCRIPTION OF DRAWINGS

FIG. 1 is a front view of a headwear for electroencephalography (hereinafter, EEG headwear) according to an exemplary embodiment of the present invention.

FIG. 2 is a view illustrating first to third arms of the EEG headwear.

FIG. 3 is another view of the first to third arms of the EEG headwear.

FIG. 4 is a view illustrating a configuration of a pad of the EEG headwear.

FIG. 5 is a perspective view of the EEG headwear.

FIG. 6 is another perspective view of the EEG headwear.

FIG. 7 is another perspective view of the EEG headwear.

FIG. 8 is another perspective view of the EEG headwear.

FIG. 9 is a view illustrating a manner of attaching a band of the EEG headwear.

FIG. 10 is a view illustrating an example of how the EEG headwear is attached.

DESCRIPTION OF EMBODIMENTS

Hereinafter, an exemplary embodiment of the invention will be described with reference to the drawings. For the purpose of clear illustration, some elements may be illustrated in a simplified manner or may be illustrated differently from actual specifications in terms of scale and/or locations.

FIG. 1 is a front view of an EEG headwear 1 according to an exemplary embodiment of the present invention, illustrating the EEG headwear 1 in an attached state. The EEG headwear 1 includes three arms (a first arm 10, a second arm 20, and a third arm 30 which will be described later with reference to FIGS. 2 and 3), and a support member 41 which is connected to the arms through bands 51, 52, 53, 54 (the support member 41 is not shown in FIG. 1, and will be described later with reference to FIGS. 5 and 6). In the following description, in a state in which the subject (wearer of the EEG headwear 1) faces to the front, as illustrated in FIG. 1, the leftward direction is defined as the −X direction, the rightward direction is defined as the +X direction, the upward direction is defined as the +Y direction, and the downward direction is defined as the −Y direction. Although not illustrated, the front direction (face side) is defined as the +Z direction, and the depth direction (occipital side) is defined as the −Z direction.

Firstly, the structured of the three arms (the first arm 10, the second arm 20, and the third arm 30) will be described with reference to FIGS. 2 and 3. FIG. 2 is a front view of the three arms as seen from an external exposed side. The first arm 10 has a base portion 11, an elastic connecting portion 12, and an electrode holding portion 13. The first arm 10 is fixed to an area extending from the vicinity of the forehead of the subject to the top of the head (see FIG. 1).

The base portion 11 is a member which is to be fixed to the vicinity of the forehead, and has through holes 111, 112 in the left and right sides in the vicinity of the forehead, respectively. The bands 51, 52 which will be described later are passed through the through holes 111, 112, respectively.

The base portion 11 may include a central processing unit (CPU) in which a wireless receiving/transmitting function is mounted, and various amplifying circuits, and the like. Therefore, the base portion 11 is preferably made of a rigid material (e.g., rigid plastic) which is excellent in waterproof performance and impact resistance.

The elastic connecting portion 12 is an elastic member which is bendable when a force is applied to it. Namely, the elastic connecting portion 12 is made of an elastic material such as elastomer, and the elasticity of the material is higher than that of the base portion 11. The elastic connecting portion 12 incorporates various cables and the like for connecting the electrode holding portion 13 to the base portion 11.

The electrode holding portion 13 is a member for fixing an EEG electrode (in the International 10/20 system, the Cz electrode) which is to be placed in the vicinity of the top of the head. The electrode holding portion 13 has two through holes 131, 132 which face the side surfaces of the head, respectively. A band 62 which will be described later is passed through the through holes 131, 132.

The second arm 20 is connected to the first arm 10, and to be fixed to one side surface (in the exemplary embodiment, the right side surface) of the head of the subject. The second arm 20 has an electrode holding portion 21 and an elastic connecting portion 22. In the exemplary embodiment, the electrode holding portion 21 has three fixing portions 211, 212, 213 (which are not shown in FIG. 2, and which will be described in detail later with reference FIG. 3) for fixing electrodes. In the example of FIG. 2, EEG electrodes 72, 73 are fixed to the electrode holding portion 21.

In the case where the electrode holding portion 21 internally has amplifying circuits and the like, similarly with the base portion 11, the electrode holding portion 21 is preferably made of a rigid material (e.g., rigid plastic) which is excellent in waterproof performance and impact resistance. In the electrode holding portion 21, a through hole 214 through which the band 51 that will be described later is to be passed is disposed in an end portion in the −Y direction. In the electrode holding portion 21, moreover, a hook 215 to which a band 62 that will be described later is to be fixed is disposed in an end portion in the +Y direction. In the electrode holding portion 21, furthermore, a hook 216 to which a band 61 that will be described later is to be fixed is disposed in the vicinity of the through hole 214 (on the −X direction side of the through hole 214). The places where the through hole 214 and the hooks 215, 216 are disposed are not limited to the illustrated places, and the hole and the hooks may be disposed in other places.

Similarly with the elastic connecting portion 12, the elastic connecting portion 22 is an elastic member which is bendable when a force is applied to it. Namely, the elastic connecting portion 22 is made of an elastic material such as elastomer, and the material is higher in elasticity than the base portion 11 and the electrode holding portion 21.

The third arm 30 is connected to the first arm 10, and to be fixed to one side surface (opposite to the side surface to which the second arm 20 is to be fixed, and, in the exemplary embodiment, the left side surface) of the head of the subject. The third arm 30 has an electrode holding portion 31 and an elastic connecting portion 32. In the exemplary embodiment, the electrode holding portion 31 has three fixing portions 311, 312, 313 (which are not shown in FIG. 2, and which will be described in detail later with reference FIG. 3) for fixing EEG electrodes. In the example of FIG. 3, EEG electrodes 75, 76 are fixed to the electrode holding portion 31.

In the case where the electrode holding portion 31 internally has amplifying circuits and the like, similarly with the base portion 11, the electrode holding portion is preferably made of a rigid material (e.g., rigid plastic) which is excellent in waterproof performance and fault resistance. In the electrode holding portion 31, a through hole 314 through which the band 52 that will be described later is to be passed is disposed in an end portion in the −Y direction. In the electrode holding portion 31, moreover, a hook 315 to which the band 62 that will be described later is to be fixed is disposed in an end portion in the +Y direction. In the electrode holding portion 31, furthermore, a hook 316 to which the band 51 that will be described later is to be fixed is disposed in the vicinity of the through hole 314 (on the +X direction side of the through hole 314). The places where the through hole 314 and the hooks 315, 316 are disposed are not limited to the illustrated places, and the hole and the hooks may be disposed in other places.

Similarly with the elastic connecting portion 12, the elastic connecting portion 32 is an elastic member which is bendable when a force is applied to it. Namely, the elastic connecting portion 32 is made of an elastic material such as elastomer, and the elasticity of the material is higher than that of the base portion 11 and the electrode holding portion 31.

The three arms will be further described with reference to FIG. 3. FIG. 3 is a front view of the three arms as seen from the side where the arms are to be contacted with the subject. A detachable pad 14 is attached to the base portion 11. In the exemplary embodiment, the pad 14 is attached to the vicinity of the surface opposed to the through holes 111, 112. The pad 14 has an arch-like shape which corresponds to the forehead of the subject. When the EEG headwear 1 is attached to the subject, the pad 14 is contacted with the vicinity of the forehead of the subject.

Referring to FIG. 4, the pad 14 will be described in detail. Preferably, the pad 14 is made of a material having a sticking property and elasticity which allow the pad to firmly contact the forehead of the subject, such as silicone. Contact surfaces 145, 146 which are to be contacted with the subject have an arch-like shape as described above.

Protruding portions 141, 142 are inserted into insertion holes (not shown) which are formed in the base portion 11. The major diameter of the protruding portion 141 is larger than the diameter of the corresponding insertion hole. The major diameter of an engaging portion 143 is smaller than the diameter of the insertion hole. Since the pad 14 is made of an elastic material such as silicone, the protruding portion 141 can be inserted into the insertion hole. In the case where the protruding portion 141 is inserted into the insertion hole, the pad 14 can be prevented from being unintentionally detached, because the major diameter of the protruding portion 141 is larger than the diameter of the insertion hole. The protruding portion 142 and an engaging portion 144 are configured in a similar manner as the protruding portion 141 and the engaging portion 143, respectively.

Referring again to FIG. 3, as described above, the pad 14 is inserted into the insertion hole (not shown) of the base portion 11, whereby the pad 14 is fixed to the base portion 11.

The electrode holding portion 13 has a fixing portion 133 to which an EEG electrode 71 is fixed (the fixing portion is not shown because of the attachment of the EEG electrode 71). The electrode holding portion 21 has the fixing portions 211, 212, 213 to which EEG electrodes 72 to 74 are fixed, respectively. Similarly, the electrode holding portion 31 has fixing portions 311, 312, 313 to which EEG electrodes 75, 76, 77 are fixed, respectively (the fixing portions 311, 313 are not shown because of the attachments of the EEG electrodes 75, 77). In FIG. 3, the example in which the three EEG electrodes 71, 75, 77 are attached is shown. For example, the fixing portions (133, 211, 212, 213, 311, 312, 313) are requested to have a shape that is similar to an insertion hole into which an electrode projection is to be inserted.

The positions where the fixing portions (133, 211, 212, 213, 311, 312, 313) are placed may be determined with reference to, for example, the International 10/20 system. Although the exemplary embodiment in which the first to third arms 10, 20, 30 have the fixing portions (133, 211, 212, 213, 311, 312, 313) for fixing the seven EEG electrodes has been described, fixing portions are not limited to the above-described configuration. The number and positions of EEG electrodes provided on the first to third arms 10, 20, 30 may be adjusted in accordance with the use.

In the electrode holding portion 21, a through hole 217 through which the band 53 that will be described later is passed through is disposed in the vicinity (on the side of the −Z direction) of the fixing portion 211. In the electrode holding portion 31, a through hole 317 through which the band 54 that will be described later is to be passed is disposed in the vicinity (on the side of the −Z direction) of the fixing portion 311. The through hole 217 may be disposed in another place of the second arm 20. Similarly, the through hole 317 may be disposed in another place of the third arm 30.

The above is the summary of the first to third arms 10, 20, 30. The attachment state of the EEG headwear 1 will be described with reference again to FIG. 1. As illustrated, the first arm 10 (the base portion 11, the pad 14, and the like) is fixed to the area extending from the vicinity of the forehead of the subject to the top of the head. The second arm 20 (the electrode holding portion 21 and the elastic connecting portion 22) is connected to the first arm 10, and fixed to the area extending to the lateral side of the head of the subject (the right side of the head). The third arm 30 (the electrode holding portion 31 and the elastic connecting portion 32) is connected to the first arm 10, and fixed to the area extending to the lateral side of the head of the subject (the left side of the head).

In the band 61 (chin band), through holes are engaged with the hooks 216, 316, respectively, thereby fixing the EEG headwear 1 to the chin of the subject. A plurality of through holes is provided in the band 61. The tightness may be adjusted by selecting the through holes to be engaged with the hooks 216, 315.

The EEG headwear 1 has the stretchable support member 41 (not shown in FIG. 1) which covers the head of the subject in a direction toward the first arm 10 (in the configuration of FIG. 1, the occipital side). The support member 41 will be described with reference to FIG. 5.

FIG. 5 is a perspective view of the EEG headwear 1 centered on the right side of the head of the subject. As illustrated, the support member 41 supports the head of the subject so as to cover a portion of the occiput. The support member 41 has a stretchable configuration. Preferably, the support member 41 has also a cushioning property. Therefore, the support member 41 may be formed by cloth or the like which has a thickness of, for example, about 2 mm to 5 mm, and in which a stretchable material is mixed.

The support member 41 is connected to the first arm 10 through the band 51, and to the second arm 20 through the band 53. The band 51 is passed through the through hole 214, then passed through the through hole 111, and, after passed through the through hole 111, folded back and fixed. As described later, the distal end of the band 51 is configured by a hook or loop fastener (described in detail later with reference to FIG. 9). The band 53 is passed through the through hole 217, and then folded back and fixed. Similarly with the band 51, the distal end of the band 53 is configured with a hook or loop fastener. The band 62 (head-top band for the top of the head) is made from a stretchable material (such as rubber), and the length of the band is adjusted by selecting holes through which the hooks 215, 315 (not shown in FIG. 5) are to be passed through. The band 62 performs fixation by pressing the electrode holding portion 13 (then, the EEG electrode 71) toward the subject (so as to press the portion against the vicinity of the top of the head). That is, the band 62 fixes a part (preferably, the vicinity of the EEG electrode 71) of the first arm 10 by pressing the first arm toward the subject. Therefore, the EEG electrode 71 can be surely fixed.

The support member 41 further has tabs 55, 56 (shown in FIG. 6) protruding in the lateral direction (X-axis direction) in a state in which the EEG headwear 1 is attached. The tab 55 is held when attaching the EEG headwear 1 to the subject. The manner of attachment will be described later with reference to FIG. 9.

FIG. 6 is a perspective view of the EEG headwear 1 centered on the left side of the head of the subject. The bands 61, 62 are preferably used for fixing the EEG headwear 1 and the electrodes, but are not essential components. Therefore, FIG. 6 shows the configuration in which the band 61 is omitted.

The support member 41 is connected to the first arm 10 through the band 52, and to the third arm 30 through the band 54. The band 52 is passed through the through hole 314 and the through hole 112, and, after passed through the through hole 112, folded back and fixed. As described later, the distal end of the band 52 is configured by a hook or loop fastener (described in detail later with reference to FIG. 9). The band 54 is passed through the through hole 317, and then folded back and fixed. Similarly with the band 51, the distal end of the band 54 is configured by a hook and loop fastener portion. The support member 41 has the tab 56 protruding in the lateral direction (X-axis direction) in a state in which the EEG headwear 1 is attached.

FIG. 7 is a perspective view of the EEG headwear 1 in which the right side of the head of the subject is set as the front. As illustrated, the pad 14 connected to the base portion 11 is fixed approximately to the forehead of the subject. As described above, the pad 14 has an arch-like shape which extends along the forehead, and made of a material (e.g., silicone) having flexibility (elasticity) and a sticking property. Therefore, the base portion 11 of the EEG headwear 1 can be firmly attached to the forehead of the subject. The tightness of the first and second arms 10, 20 is adjusted by adjusting the lengths of the folded parts of the bands 51, 53.

FIG. 8 is a perspective view of the EEG headwear 1 in which the left side of the head of the subject is set as the front. Similarly with the configuration shown in FIG. 7, the base portion 11 of the EEG headwear 1 can be firmly attached to the forehead of the subject by the pad 14. The tightness of the first and third arms 10, 30 is adjusted by adjusting the lengths of the folded parts of the bands 52, 54.

As shown in FIG. 8, an electrode connecting portion 113 may be disposed in the base portion 11. In the above description, the EEG headwear 1 for fixing seven EEG electrodes has been described. There is a possibility that the number of necessary EEG electrodes is increased depending on the condition of the subject and the object of the measurement. The electrode connecting portion 113 is a connecting portion (cable insertion port) for acquiring a measurement signal from an EEG electrode which is required in accordance with the object of the measurement. In FIG. 8, the electrode connecting portion 113 is connected to an EEG electrode 78 having a seal-like shape, through a cable. Although, in the example of FIG. 8, only the single electrode connecting portion 113 is shown, the base portion 11 may have a plurality of electrode connecting portions 113, or a cable insertion port may be disposed not only in the base portion 11 but also in the electrode holding portions 21, 31 and the electrode holding portion 13.

Adjustment of the tightness of the first to third arms 10, 20, 30 by the bands 51, 52, 53, 54 will be described with reference to FIG. 9. FIG. 9 is an enlarged view conceptually showing the adjustment of the second arm 20 by the band 53. In FIG. 9, for the purpose of clear illustration, portions other than the band 53 and the through hole 217 are illustrated in a simplified manner.

In the above-described configuration, the bands 51, 52, 53, 54 function as an adjusting mechanism for adjusting the degrees of fixations of the first to third arms 10, 20, 30 to the head of the subject. In the exemplary embodiment, namely, the EEG headwear 1 has a configuration including four adjusting mechanisms (the bands 51, 52, 53, 54). In other words, the adjusting mechanisms are disposed in the bands 51, 52, 53, 54 for connecting the support member 41 with the first to third arms 10, 20, 30, respectively. Hereinafter, the functions of the adjusting mechanisms will be described with exemplifying the band 53.

The band 53 has a surface on which fiber hooks are raised (a hook fiber surface 531), and a surface on which fiber loops are raised (a loop fiber surface 532) on the same surface. In the exemplary embodiment, the hook fiber surface 531 is disposed in the distal end portion of the band 53. Alternatively, the loop fiber surface 532 may be disposed in the distal end portion of the band 53.

The band 53 is a hook and loop fastener in which, after passed through the through hole 217, the distal end of the band 53 is folded back and fixed. Hereinafter, the adjusting method will be described in detail. Firstly, the user (the doctor, the nurse, or the like) passes the distal end (the vicinity of the hook fiber surface 531) of the band 53 through the through hole 217. Thereafter, the user nips the distal end of the band 53 with fingers F1, F2, and pulls the band while checking the attachment state of the EEG headwear 1. After the user considers that the attachment state is appropriate, the user folds back the band 53. The user causes the hook fiber surface 531 to stick to the loop fiber surface 532, thereby adjusting the folded length of the band 53. The state where the hook fiber surface 531 and the loop fiber surface 532 stick together is shown in, for example, FIG. 5. The longer the folded length, the greater the tightness of the second arm 20 (and the first arm 10 connected to the second arm 20). The shorter the folded length, the lesser the tightness of the second arm 20 (and the first arm 10 connected to the second arm 20). The tightness is adjusted so that the EEG headwear 1 is attached to the head of the subject with tightness suitable for the size of the head.

The above-described fixation using a hook and loop fastener is a mere example, and a similar adjustment may be performed by using a button and buttonholes. For example, a plurality of buttonholes may be disposed in the distal end side of the band 53, and a button may be disposed in the root side (the side which is connected to the support member 41) of the band 53. The user (the doctor, the nurse, or the like) selects one of the buttonholes through which the button is to be passed, thereby adjusting the folded length of the band 53.

Although not illustrated, the degrees of fixations of the first to third arms 10, 20, 30 to the head of the subject by the bands 51, 52, 54 are adjusted in a method similar to that described above.

The bands 51, 52, 53, 54 are examples of the adjusting mechanism for adjusting the tightness of the first to third arms 10, 20, 30. The tightness may be adjusted by means other than bands. For example, an adjusting mechanism similar to a usual belt buckle may be disposed in an approximately middle portion (the vicinity of the center of the occipital side of the subject) of the support member 41. In this case, the bands 51, 52, 53, 54 may be fixed by, after passed through the respective through holes (111, 112, 217, 317), for example, being sewn together.

The above-described EEG headwear 1 may be used in a usual EEG test, and is particularly effective also in the case where it is used in the field of emergency medicine.

Therefore, an example in which the EEG headwear 1 is used on an emergency patient will be described with reference to FIG. 10.

It is assumed that the subject is lying on a placement surface G, i.e., the subject is an emergency patient. The placement surface G is mainly a bed in a hospital, the mattress of a stretcher, or the like.

Firstly, the user (the doctor, the nurse, or the like) attaches the EEG electrodes 71 to 78 to the EEG headwear. In a situation where the head of the subject is placed on the placement surface G, then, the first to third arms 10, 20, 30 are caused to approach the head of the subject. In this case, the pad 14 is fixed so as to be contacted with the vicinity of the forehead of the subject. Then, the user slightly lifts the head of the subject, and, in this state, places the support member 41 between the head and the placement surface G. Here, the user is requested to support the head of the subject with one hand, and sequentially pull the tab 55 (not shown) and the tab 56 in the −Y direction (toward the chin of the subject) with the other hand. The tabs 55, 56 are provided to protrude in the X-axis direction from the support member 41. That is, the tabs 55, 56 are easily projected from the head of the subject. The tabs 55, 56 are pulled in a sliding manner toward the chin, thereby setting a state where the EEG headwear 1 covers the head of the subject.

As described above, the pad 14 is preferably made of an elastic material such as silicone, and has an arch-like shape which extends along the forehead of the subject. (FIG. 4). Even when the support member 41 is slid in the −Y direction (toward the chin of the subject) by using the tabs 55, 56, therefore, the pad 14 is in a state where it remains to be in close contact with the vicinity of the forehead of the subject while slightly changing the angle. That is, the pad 14 functions to prevent positional displacement of the base portion 11 from occurring. Therefore, the support member 41 can be easily set to a predetermined position, and the work to again adjust the position of the base portion 11 can be reduced.

The user sets the support member 41 between the placement surface G and the head, and then adjusts the folded lengths of the bands 51, 52, 53, 54 (FIG. 9). This adjustment adjusts the degrees of fixations of the first to third arms 10, 20, 30 to the head of the subject. After the adjustments of the folded lengths, the bands 61, 62 may be attached. Alternatively, the bands 61, 62 may be previously attached to hooks 215, 216, 315, 316 before the EEG headwear 1 is attached to the subject. After the above-described attachment process, the user starts the EEG measurement.

Advantages of the EEG headwear 1 according to the exemplary embodiment will be described. The support member 41 is connected to the first to third arms 10, 20, 30, and covers a portion (in the above-described example, the occiput) of the head by the stretchable material. Since the head is covered by the stretchable support member 41, EEG electrodes can be approximately fixed to predetermined positions when the EEG headwear 1 is attached. Moreover, the EEG headwear 1 has the adjusting mechanism (in the above-described example, the bands 51, 52, 53, 54) for adjusting the tightness of the first to third arms 10, 20, 30. By adjusting the tightness by the adjusting mechanism, the EEG electrodes can be firmly attached to suitable locations on the head of the subject. In other words, the EEG electrodes can be firmly attached at suitable positions with suitable force irrespective of the size of the head of the subject.

As described above, preferably, the adjusting mechanism may be disposed in each of the bands 51, 52, 53, 54 for connecting the first to third arms 10, 20, 30 together. In the configuration where the adjusting mechanisms are disposed in the connecting portions of the support member 41 and the arms as described above, it is possible to avoid a situation where only one arm is strongly fastened, and the arms can be uniformly fixed with suitable force.

Preferably, the adjusting mechanism is configured by a folding hook and loop fastener (the hook fiber surface 531 and the loop fiber surface 532) as shown in FIG. 9. Such hook and loop fasteners can be adjusted in length in a very easy manner, and are used in many products or the like. Also in a scene of emergency medical service or the like, therefore, EEG electrodes can be attached adequately and quickly.

The band 62 (band for the top of the head) fixes the electrode holding portion 13 to the vicinity of the top of the head of the subject. According to the configuration, the EEG electrode 71 in the vicinity of the top of the head can be firmly attached.

The band 61 (chin band) fixes together the EEG headwear 1 and the vicinity of the chin of the subject. According to the configuration, the EEG headwear 1 can be firmly attached to the subject.

The pad 14 is attached to the first arm 10. The pad 14 has an arch-like shape which allows the pad to firmly contact the head of the subject, and further has elasticity. In the process of attaching the EEG headwear 1, therefore, the first arm 10 can be appropriately fixed to the head of the subject.

Each of the arms has the rigid electrode holding portion (the base portion 11, or the electrode holding portion 13, 21, 31) and the elastic connecting portion (12, 22, 32). Since the arms have the elastic connecting portions (12, 22, 32), respectively, the arms are fixed in a shape conforming to the shape of the head of the subject. Since the electrode holding portions (the base portion 11 and the electrode holding portions 13, 21, 31) have rigidity, the internal electronic circuits and the like can be protected from impact and the like.

The rigid electrode holding portions (the base portion 11 and the electrode holding portions 13, 21, 31) may have the electrode connecting portion 113 configured to receive a measurement signal from another EEG electrode through a cable (FIG. 8).

According to the configuration, the number of used EEG electrodes can be flexibly changed in accordance with the measurement contents.

The support member 41 has the tabs 55, 56 protruding in the lateral direction (X-axis direction) of the subject. The user holds the tabs 55, 56 and moves them in a sliding manner, whereby the support member 41 is firmly attached to the head of the subject in an easy manner.

While the present invention has been described with reference to a certain exemplary embodiment thereof, the scope of the present invention is not limited to the exemplary embodiment described above, and it will be understood by those skilled in the art that various changes and modifications may be made therein without departing from the scope of the present invention as defined by the appended claims.

Although, in the above description, it is assumed that the base portion 11 has a wireless communication function, the invention is not limited to this. A configuration in which cables elongate from the EEG electrodes to an electroencephalograph may be employed.

Although, in the above description, it is assumed that the first arm 10 is fixed to an area extending from the vicinity of the forehead to the top of the head, the invention is not limited to this. Depending on the use, namely, the first arm 10 may be fixed to an area extending from the occiput to the top of the head. In this case, the support member 41 covers the vicinity of the forehead. That is, the support member 41 may have a configuration in which it covers a portion of the head of the subject in a direction toward to the first arm 10.

The shapes of the base portion 11 and the electrode holding portion 21, 31 are mere examples. The electrode holding portion 21, 31 may not have the above-described substantially T-like shape, and instead may have another shape.

Information indicating the operation sequence may be indicated on the bands 51, 52, 53, 54, 55, 56, 61. For example, "2" may be indicated on the band 51, "2" may be indicated on the band 52, "3" may be indicated on the band 53, "3" may be indicated on the band 54, "1" may be indicated on the band 55, "1" may be indicated on the band 56, and "4" may be indicated on the band 61. According to the configuration, the user can quickly attach the EEG headwear 1 to the subject without mistaking the operation procedure.

This application is based on Japanese Patent Application No. 2015-103603 filed on May 21, 2015, the entire content of which is incorporated herein by reference.

The invention claimed is:

1. A headwear for electroencephalography, the headwear comprising:
   a first arm to be attached to an area extending from a forehead or an occiput of a subject to a top of a head of the subject, the first arm comprising a first electrode holding portion being configured to hold at least a first electroencephalogram electrode;
   a second arm to be attached to a lateral side of the head of the subject, the second arm being connected to the first arm and the second arm comprising a second electrode holding portion configured to hold at least a second electroencephalogram electrode;
   a third arm to be attached to another lateral side of the head of the subject, the third arm being connected to the first arm and the third arm comprising a third electrode holding portion configured to hold at least a third electroencephalogram electrode; and
   a stretchable support member connectable to the second arm and the third arm to cover at least a portion of the head of the subject, the stretchable support member comprising at least one adjusting mechanism configured to adjust tightness of the headwear to the head, wherein the first arm comprises a rigid portion configured to be fixed at the forehead of the subject.

2. The headwear according to claim 1, wherein the at least one adjusting mechanism comprises a plurality of bands that connects the stretchable support member to the second arm and the third arm.

3. The headwear according to claim 2, wherein the plurality of bands is configured such that a distal end of each band of the plurality of bands is passed through a corresponding through hole provided in the second arm and the third arm.

4. The headwear according to claim 2, wherein the second arm and the third arm comprise a plurality of through holes through which the plurality of bands is inserted.

5. The headwear according to claim 4, wherein each band of the plurality of bands comprises a hook and loop fastener having a hook fiber surface and a loop fiber surface, one of the hook fiber surface and the loop fiber surface being provided at a distal end of the band.

6. The headwear according to claim 1, further comprising a head-top band that is connected to the second arm and the third arm to hold a portion of the first arm toward the subject.

7. The headwear according to claim 6, wherein the first arm comprises at least one through hole through which the head-top band is inserted.

8. The headwear according to claim 6, wherein the head-top band is stretchable.

9. The headwear according to claim 1, further comprising a chin band that is connected to the second arm and the third arm to be firmly attached to a chin of the subject.

10. The headwear according to claim 1, wherein the first arm further comprises an elastic pad having an arch-like shape that corresponds to the forehead of the subject.

11. The headwear according to claim 1, wherein the stretchable support member comprises tabs protruding in a lateral direction of the head of the subject.

12. The headwear according to claim 1, wherein the rigid portion comprises a first rigid base portion,
wherein the first electrode holding portion comprises a first rigid electrode holding portion to which the first electroencephalogram electrode is fixed and the first arm further comprises a first elastic connecting portion connecting the first electrode holding portion to the first rigid base portion,
wherein the second arm comprises a second rigid base portion configured to be fixed the lateral side of the head of the subject,
wherein the third arm comprises a third rigid base portion configured to be fixed at the other lateral side of the head of the subject that opposes the lateral side of the head of the subject,
wherein the second electrode holding portion comprises a second rigid electrode holding portion to which the second electroencephalogram electrode is fixed and the second arm further comprises a second elastic connecting portion connecting the second electrode holding portion to the second rigid base portion, and
wherein the third electrode holding portion comprises a third rigid electrode holding portion to which the third electroencephalogram electrode is fixed and the third arm further comprises a third elastic connecting portion connecting the third electrode holding portion to the third rigid base portion.

13. The headwear according to claim 12, wherein the first rigid electrode holding portion, the second rigid electrode holding portion, and the third rigid electrode holding portion respectively comprise an electrode connecting portion configured to receive a first measurement signal, a second measurement signal, and a third measurement signal from the respective first electroencephalogram electrode, the second electroencephalogram, and the third electroencephalogram electrode.

14. The headwear according to claim 1, wherein information indicating an operation sequence of the at least one adjusting mechanism is indicated on the headwear.

15. The headwear according to claim 1, wherein the first arm, the second arm, and the third arm are configured to hold the first electroencephalogram electrode, the second electroencephalogram electrode, and the third electroencephalogram electrode at positions determined based on the International 10/20 system.

16. The headwear according to claim 1, wherein at least one of the second arm and the third arm comprises a second rigid portion configured to be fixed at the lateral side or the other lateral side of the head of the subject.

17. The headwear according to claim 1, wherein the rigid portion is configured to extend from the forehead to top of the head of the subject.

18. The headwear according to claim 1, wherein at least one of the second arm and the third arm comprises a second rigid portion.

* * * * *